United States Patent [19]

Lunkenheimer et al.

[11] Patent Number: 5,583,151

[45] Date of Patent: Dec. 10, 1996

[54] PYRIDINE-4-CARBOXAMIDE COMPOUNDS WHICH ARE USEFUL FOR PROTECTING PLANTS AGAINST DISEASE

[75] Inventors: Winfried Lunkenheimer, Wuppertal; Heinz-Wilhelm Dehne, Monheim; Stefan Dutzmann, Hilden; Gerd Hänssler, Leverkusen; Uta Schulz, Leichlingen, all of Germany

[73] Assignee: Bayer Aktiengesellschaft, Leverkusen, Germany

[21] Appl. No.: 240,771

[22] PCT Filed: Nov. 6, 1992

[86] PCT No.: PCT/EP92/02556

§ 371 Date: May 12, 1994

§ 102(e) Date: May 12, 1994

[87] PCT Pub. No.: WO93/10095

PCT Pub. Date: May 27, 1993

[30] Foreign Application Priority Data

Nov. 19, 1991 [DE] Germany .................... 41 38 026.6

[51] Int. Cl.⁶ .................... C07D 213/81; A01N 43/40
[52] U.S. Cl. .................... 514/354; 546/323
[58] Field of Search .................... 546/283, 324, 546/323; 514/336, 354

[56] References Cited

U.S. PATENT DOCUMENTS 3,398,155  8/1968  Horrom .................... 546/323

*Primary Examiner*—Zinna Northington Davis
*Attorney, Agent, or Firm*—Sprung Horn Kramer & Woods

[57] ABSTRACT

New substituted pyridine-4-carboxamides of the formula

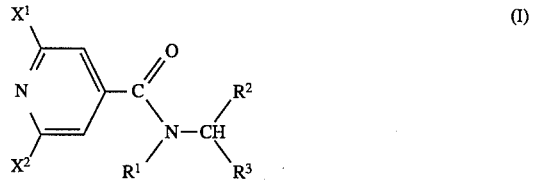

in which $R^1$, $R^2$, $R^3$, $X^1$ and $X^2$ have the meanings given in the description, a plurality of processes for the preparation of these substances, and their use for generating resistance in plants against attack by undesired microorganisms.

5 Claims, No Drawings

PYRIDINE-4-CARBOXAMIDE COMPOUNDS WHICH ARE USEFUL FOR PROTECTING PLANTS AGAINST DISEASE

This application is a 371 of PCT92/02556 filed Nov. 6, 1992.

The invention relates to new substituted pyridine-4-carboxamides, to a plurality of processes for their preparation, and to their use for the generation of resistance in plants against attack by undesired microorganisms.

It is known that certain pyridine-4-carboxylic acid derivatives can be used for generating resistance in plants against attack by phytopathogenic microorganisms (cf. EP-OS (European Published Specification) 0,268,775). 2,6-Dichloropyridine-4-carboxylic acid, methyl 2,6-dichloropyridine-4-carboxylate and α-(4-chlorophenyl)benzyl 2,6-dichloropyridine-4-carboxylate, for example, can be used for the abovementioned purpose. However, the activity of these substances is not always satisfactory, in particular when low application rates are used.

New substituted pyridine-4-carboxamides of the formula

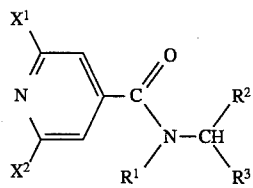  (I)

in which
$R^1$ represents hydrogen or alkyl,
$R^2$ represents hydrogen or alkyl,
$R^3$ represents a radical of the formula

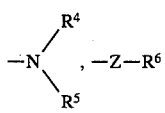

or $-SO_2-R^7$, where $R^4$ represents hydrogen, optionally substituted alkyl, optionally substituted alkenyl, optionally substituted alkinyl, optionally substituted cycloalkyl, optionally substituted cycloalkenyl, optionally substituted alkoxy, optionally substituted alkanoyl or optionally substituted alkoxycarbonyl, $R^5$ represents hydrogen, optionally substituted alkyl, optionally substituted alkanoyl, optionally substituted aroyl, optionally substituted heteroarylcarbonyl, optionally substituted alkoxycarbonyl, optionally substituted alkylsulphonyl or optionally substituted arylsulphonyl, or $R^4$ and $R^5$ together with the nitrogen atom to which they are bonded represent an optionally substituted heterocycle, $R^6$ represents hydrogen, optionally substituted alkyl, optionally substituted alkenyl, optionally substituted alkinyl, optionally substituted alkanoyl, optionally substituted cycloalkyl, optionally substituted cycloalkenyl, optionally substituted aryl, optionally substituted arylcarbonyl, optionally substituted heterocyclyl or optionally substituted heterocyclylcarbonyl, $R^7$ represents optionally substituted aryl and
Z represents oxygen or sulphur, or
$R^2$ and $R^3$ together with the carbon atom to which they are bonded represent an optionally substituted five- or six-membered ring which can contain one or two hetero atoms, one or two keto groups and an $SO_2$ group,
$X^1$ represents halogen and
$X^2$ represents halogen, have now been found.

Depending on the nature of the substituents, the compounds of the formula (I) can exist in the form of geometric and/or optical isomers or variously composed isomer mixtures. The invention relates to the pure isomers and to the isomer mixtures.

Furthermore, it has been found that substituted pyridine-4-carboxamides of the formula (I) are obtained when
a) pyridine-4-carboxamides of the formula

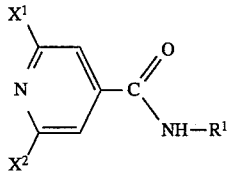  (II)

in which
$R^1$, $X^1$ and $X^2$ have the abovementioned meaning, are reacted with compounds of the formula

  (III)

in which
$R^2$ and $R^3$ have the abovementioned meaning and
$E^1$ represents a suitable leaving group,
if appropriate in the presence of a diluent and if appropriate in the presence of a reaction auxiliary, or
b) pyridine-4-carboxamides of the formula

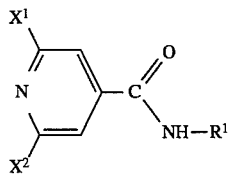  (II)

in which
$R^1$, $X^1$ and $X^2$ have the abovementioned meaning, are reacted with aldehydes of the formula

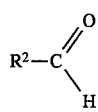  (IV)

in which
$R^2$ has the abovementioned meaning,
if appropriate in the presence of a diluent and if appropriate in the presence of a reaction auxiliary, or
c) substituted pyridine-4-carboxamides of the formula

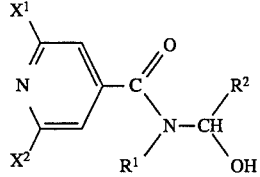  (Ia)

in which
$R^1$, $R^2$, $X^1$ and $X^2$ have the abovementioned meaning, are reacted either
α) with carbinols or mercaptans of the formula

$R^8-Z-H$  (V)

in which
Z has the abovementioned meaning and $R^8$ represents optionally substituted alkyl, optionally substituted alkenyl, optionally substituted alkinyl, optionally substituted alkanoyl, optionally substituted cycloalkyl, optionally substituted cycloalkenyl, optionally substituted aryl, optionally substituted arylcarbonyl, optionally substituted heterocyclyl or optionally substituted heterocyclylcarbonyl, if appropriate in the presence of a diluent and if appropriate in the presence of a reaction auxiliary, or β) with acid anhydrides of the formula

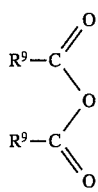
(VI)

in which $R^9$ represents optionally substituted alkyl, optionally substituted aryl or optionally substituted heterocyclyl, if appropriate in the presence of a diluent and if appropriate in the presence of a reaction auxiliary, or γ) with amines of the formula

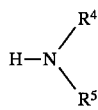
(VII)

in which $R^4$ and $R^5$ have the abovementioned meaning, or with sulphinic acid derivatives of the formula $R^7\text{-}SO_2\text{-}X$ (VIII)

in which $R^7$ has the abovementioned meaning and

X represents an alkali metal atom or hydrogen, if appropriate in the presence of a diluent and if appropriate in the presence of a reaction auxiliary, or d) pyridine-4-carboxamide derivatives of the formula

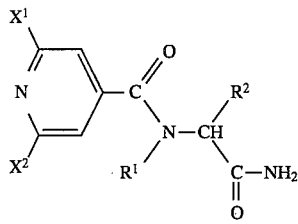
(IX)

in which $R^1$, $R^2$, $X^1$ and $X^2$ have the abovementioned meaning, are reacted with alcohols of the formula, $R^{10}\text{-OH}$ (X)

in which $R^{10}$ represents alkyl, in the presence of an oxidant and if appropriate in the presence of a diluent, or e) pyridine-4-carboxylic acid derivatives of the formula

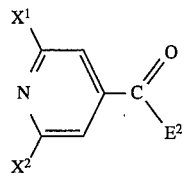
(XI)

in which $X^1$ and $X^2$ have the abovementioned meaning and $E^2$ represents a suitable leaving group, are reacted with amines of the formula

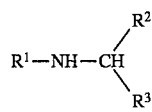
(XII)

in which $R^1$, $R^2$ and $R^3$ have the abovementioned meaning, if appropriate in the presence of a diluent and if appropriate in the presence of a reaction auxiliary and, if substituted pyridine-4-carboxamides were in this case prepared in which $R^3$ represents hydroxyl, the products are, if appropriate, subsequently reacted with an acylating agent or sulphonating agent, if appropriate in the presence of a diluent and if appropriate in the presence of a reaction auxiliary.

Finally, it has been found that the new substituted pyridine-4-carboxamides of the formula (I) are very useful for the generation of resistance in plants against attack by undesired microorganisms.

Surprisingly, the substituted pyridine-4-carboxamides of the formula (I) according to the invention are more suitable for generating resistance against attack by phytopathogenic microorganisms than 2,6-dichloropyridine-4-carboxylic acid, methyl 2,6-dichloropyridine-4-carboxylate and α-(4-chlorophenyl)-benzyl 2,6-dichloropyridine-4-carboxylate, which are substances known from the prior art having a similar constitution and the same direction of action.

Formula (I) provides a general definition of the substituted pyridine-4-carboxamides according to the invention.

$R^1$ preferably represents hydrogen or straight-chain or branched alkyl having 1 to 6 carbon atoms.

$R^2$ preferably represents hydrogen or straight-chain or branched alkyl having 1 to 6 carbon atoms.

$R^3$ represents a radical of the formula

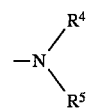
(VII)

$R^4$ preferably represents hydrogen, straight-chain or branched alkyl having 1 to 6 carbon atoms, straight-chain or branched alkenyl having 2 to 6 carbon atoms, straight-chain or branched alkinyl having 2 to 6 carbon atoms, straight-chain or branched hydroxyalkyl having 1 to 6 carbon atoms, straight-chain or branched alkoxyalkyl having 1 to 6 carbon atoms in the alkyl moiety and 1 to 6 carbon atoms in the alkoxy moiety, alkanoyl having 1 to 6 carbon atoms in the alkane moiety, alkoxycarbonyl having 1 to 6 carbon atoms in the alkoxy moiety, alkoxy having 1 to 6 carbon atoms, formyl, cycloalkyl having 3 to 7 carbon atoms or cycloalkenyl having 3 to 7 carbon atoms.

$R^5$ preferably represents hydrogen, straight-chain or branched alkyl having 1 to 6 carbon atoms, straight-chain or branched hydroxyalkyl having 1 to 6 carbon atoms, straight-chain or branched alkoxyalkyl having 1 to 6 carbon atoms in the alkoxy moiety and 1 to 6 carbon atoms in the alkyl moiety, alkanoyl having 1 to 6 carbon atoms in the alkane moiety, alkylsulphonyl having 1 to 6 carbon atoms in the alkyl moiety, alkoxycarbonyl having 1 to 6 carbon atoms in the alkoxy moiety, formyl, straight-chain or branched halogenoalkanoyl having 2 to 7 carbon atoms and 1 to 13 identical or different halogen atoms, arylcarbonyl having 6 to 10 carbon atoms in the aryl moiety, which can be monosubstituted to trisubstituted by identical or different substituents from the series comprising halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogeno alkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or by phenyl which, in turn, can be monosubstituted to trisubstituted by identical or different substituents from the series comprising halogen and/or alkyl having 1 to 4 carbon atoms, or $R^5$ preferably represents arylsulphonyl having 6 to 10 carbon atoms in the aryl moiety, which can be monosubstituted to trisubstituted by identical or different substituents from the series comprising halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogeno alkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or by phenyl which, in turn, can be monosubstituted to trisubstituted by identical or different substituents from the series comprising halogen and/or alkyl having 1 to 4 carbon atoms, or $R^5$ preferably represents heteroarylcarbonyl having 2 to 9 carbon atoms and 1 to 4 hereto atoms, such as nitrogen, oxygen or sulphur, it being possible for the heterocycle to be monosubstituted to trisubstituted by identical or different substituents from the series comprising halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or by phenyl which, in turn, can be monosubstituted to trisubstituted by identical or different substituents from the series comprising halogen and/or alkyl having 1 to 4 carbon atoms.

$R^4$ and $R^5$ together with the nitrogen atom to which they are bonded also preferably represent a saturated six-membered heterocycle which can contain a further hetero atom, such as nitrogen, oxygen or sulphur, and/or 1 or 2 keto groups, and which is optionally monosubstituted to trisubstituted by straight-chain or branched alkyl having 1 to 4 carbon atoms.

$R^6$ preferably represents hydrogen, straight-chain or branched alkyl having 1 to 6 carbon atoms, straight-chain or branched alkenyl having 2 to 6 carbon atoms, straight-chain or branched alkinyl having 2 to 6 carbon atoms, straight-chain or branched hydroxyalkyl having 1 to 6 carbon atoms, straight-chain or branched alkoxyalkyl having 1 to 6 carbon atoms in the alkoxy moiety and 1 to 6 carbon atoms in the alkyl moiety, alkanoyl having 1 to 6 carbon atoms in the alkane moiety, alkoxycarbonyl having 1 to 6 carbon atoms in the alkoxy moiety, straight-chain or branched halogenoalkyl having 1 to 6 carbon atoms and 1 to 13 identical or different halogen atoms, formyl, cycloalkyl having 3 to 7 carbon atoms, cycloalkenyl having 3 to 7 carbon atoms, arylalkyl having 1 to 6 carbon atoms in the straight-chain or branched alkyl moiety and 6 to 10 carbon atoms in the aryl moiety, which can be monosubstituted to trisubstituted by identical or different substituents from the series comprising halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or by phenyl which, in turn, can be monosubstituted to trisubstituted by identical or different substituents from the series comprising halogen and/or alkyl having 1 to 4 carbon atoms, or $R^6$ preferably represents arylcarbonyl having 6 to 10 carbon atoms in the aryl moiety, which can be monosubstituted to trisubstituted by identical or different substituents from the series comprising halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoxyliminoalkyl having 1 to 4 carbon atoms in the alkoxy moiety and 1 to 4 carbon atoms in the alkyl moiety, and/or by phenyl which, in turn, can be monosubstituted to trisubstituted by identical or different substituents from the series comprising halogen and/or alkyl having 1 to 4 carbon atoms, or $R^6$ preferably represents aryl having 6 to 10 carbon atoms which can be monosubstituted to trisubstituted by identical or different substituents from the series comprising halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or by phenyl which, in turn, can be monosubstituted to trisubstituted by identical or different substituents from the series comprising halogen and/or alkyl having 1 to 4 carbon atoms, or $R^6$ preferably represents heterocyclylalkyl having 1 to 6 carbon atoms in the straight-chain or branched alkyl radical and 2 to 9 carbon atoms and 1 to 4 identical or different hetero atoms, such as nitrogen, oxygen and/or sulphur, in the heterocycle, which can be monosubstituted to trisubstituted by identical or different substituents from the series comprising halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or by phenyl which, in turn, can be monosubstituted to trisubstituted by identical or different substituents from the series comprising halogen and/or alkyl having 1 to 4 carbon atoms, or $R^6$ preferably represents heterocyclylcarbonyl having 2 to 9 carbon atoms and 1 to 4 identical or different hetero atoms, such as nitrogen, oxygen and/or sulphur, in the heterocycle, which can be monosubstituted to trisubstituted by identical or different substituents from the series comprising halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or by phenyl which, in turn, can be monosubstituted to trisubstituted by identical or different substituents from the series comprising halogen and/or alkyl having 1 to 4 carbon atoms, or $R^6$ preferably represents heterocyclyl having 2 to 9 carbon atoms and 1 to 4 identical or different hetero atoms, such as nitrogen, oxygen and/or sulphur, in the heterocycle, which can be monosubstituted to trisubstituted by identical or different substituents from the series comprising halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or by phenyl which, in turn, can be monosubstituted to trisubstituted by identical or different substituents from the series comprising halogen and/or alkyl having 1 to 4 carbon atoms.

$R^7$ preferably represents aryl having 6 to 10 carbon atoms which can be monosubstituted to trisubstituted by identical or different substituents from the series comprising halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or by phenyl which, in turn, can be monosubstituted to trisubstituted by identical or different substituents from the series comprising halogen and/or alkyl having 1 to 4 carbon atoms.

$R^2$ and $R^3$ together with the carbon atom to which they are bonded also preferably represent a five- or six-membered ring which can contain one or two hereto atoms, such as nitrogen, oxygen and/or sulphur, one or two keto groups and an $SO_2$ group, and which is optionally substituted by alkyl having 1 to 4 carbon atoms or a fused benzene ring.

Z represents oxygen or sulphur.

$X^1$ preferably represents fluorine, chlorine, bromine or iodine.

$X^2$ preferably represents fluorine, chlorine, bromine or iodine.

$R^1$ particularly preferably represents hydrogen or straight-chain or branched alkyl having 1 to 4 carbon atoms.

$R^2$ particularly preferably represents hydrogen or straight-chain or branched alkyl having 1 to 4 carbon atoms.

$R^3$ represents a radical of the formula $$-N{\Large\diagup}^{R^4}_{\diagdown R^5},$$

-Z-$R^6$ or -$SO_2$-$R^7$.

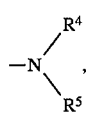

$R^4$ particularly preferably represents hydrogen, straight-chain or branched alkyl having 1 to 4 carbon atoms, straight-chain or branched alkenyl having 2 to 4 carbon atoms, straight-chain or branched alkinyl having 2 to 4 carbon atoms, straight-chain or branched hydroxyalkyl having 1 to 4 carbon atoms, straight-chain or branched alkoxyalkyl having 1 to 4 carbon atoms in the alkyl moiety and 1 to 4 carbon atoms in the alkoxy moiety, alkanoyl having 1 to 4 carbon atoms in the alkane moiety, alkoxycarbonyl having 1 to 4 carbon atoms in the alkoxy moiety, alkoxy having 1 to 4 carbon atoms, formyl, cycloalkyl having 3 to 6 carbon atoms or cycloalkenyl having 3 to 6 carbon atoms.

$R^5$ particularly preferably represents hydrogen, straight-chain or branched alkyl having 1 to 4 carbon atoms, straight-chain or branched hydroxyalkyl having 1 to 4 carbon atoms, straight-chain or branched alkoxyalkyl having 1 to 4 carbon atoms in the alkoxy moiety and 1 to 4 carbon atoms in the alkyl moiety, alkanoyl having 1 to 4 carbon atoms in the alkane moiety, alkylsulphonyl having 1 to 4 carbon atoms, alkoxycarbonyl having 1 to 4 carbon atoms in the alkoxy moiety, formyl, straight-chain or branched halogenoalkanoyl having 2 to 5 carbon atoms and 1 to 9 identical or different halogen atoms, phenylcarbonyl which can be monosubstituted to trisubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoxyiminomethyl, ethoximinoethyl and/or phenyl, which, in turn, can be monosubstituted to trisubstituted by identical or different substituents from the series comprising fluorine, chlorine, bromine, methyl and/or ethyl, or $R^5$ particularly preferably represents phenylsulphonyl which can be monosubstituted to trisubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoxyiminomethyl, ethoximinoethyl and/or phenyl, which, in turn, can be monosubstituted to trisubstituted by identical or different substituents from the series comprising fluorine, chlorine, bromine, methyl and/or ethyl, or $R^5$ particularly preferably represents heteroarylcarbonyl having 2 to 9 carbon atoms and 1 to 3 hetero atoms, such as nitrogen, oxygen and sulphur, it being possible for the heterocycle to be monosubstituted to trisubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl, which, in turn, can be monosubstituted to trisubstituted by identical or different substituents from the series comprising fluorine, chlorine, bromine, methyl and/or ethyl.

$R^4$ and $R^5$ together with the nitrogen atom to which they are bonded also particularly preferably represent a saturated six-membered heterocycle which can contain a further hetero atom, such as nitrogen, oxygen or sulphur, and/or 1 or 2 keto groups, and which is optionally monosubstituted to trisubstituted by straight-chain or branched alkyl having 1 to 4 carbon atoms.

$R^6$ particularly preferably represents hydrogen, straight-chain or branched alkyl having 1 to 4 carbon atoms, straight-chain or branched alkenyl having 2 to 4 carbon atoms, straight-chain or branched alkinyl having 2 to 4 carbon atoms, straight-chain or branched hydroxyalkyl having 1 to 4 carbon atoms, straight-chain or branched alkoxyalkyl having 1 to 4 carbon atoms in the alkoxy moiety and 1 to 4 carbon atoms in the alkyl moiety, alkanoyl having 1 to 4 carbon atoms in the alkane moiety, alkoxycarbonyl having 1 to 4 carbon atoms in the alkoxy moiety, straight-chain or branched halogenoalkyl having 1 to 4 carbon atoms and 1 to 9 identical or different halogen atoms, formyl, cycloalkyl having 3 to 6 carbon atoms, cycloalkenyl having 3 to 6 carbon atoms, phenylalkyl having 1 to 4 carbon atoms in the straight-chain or branched alkyl moiety, it being possible for the phenyl moiety to be monosubstituted to trisubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl, which, in turn, can be monosubstituted to trisubstituted by identical or different substituents from the series comprising fluorine, chlorine, bromine, methyl and/or ethyl, or $R^6$ particularly preferably represents phenylcarbonyl which can be monosubstituted to trisubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl, which, in turn, can be monosubstituted to trisubstituted by identical or different substituents from the series comprising fluorine, chlorine, bromine, methyl and/or ethyl, or $R^6$ particularly preferably represents phenyl which can be monosubstituted to trisubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl, which, in turn, can be monosubstituted to trisubstituted by identical or different substituents from the series comprising fluorine, chlorine, bromine, methyl and/or ethyl, or $R^6$ particularly preferably represents heterocyclylalkyl having 1 to 4 carbon atoms in the straight-chain or branched alkyl radical and 2 to 9 carbon atoms and 1 to 3 identical or different hereto atoms, such as nitrogen, oxygen and/or sulphur, in the heterocycle, which can be monosubstituted to trisubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl, which, in turn, can be monosubstituted to trisubstituted by identical or different substituents from the series comprising fluorine, chlorine, bromine, methyl and/or ethyl, or $R^6$ particularly preferably represents heterocyclylcarbonyl having 2 to 9 carbon atoms and 1 to 3 identical or different hetero atoms, such as nitrogen, oxygen and/or sulphur, in the heterocycle, which can be monosubstituted to trisubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl, which, in turn, can be monosubstituted to trisubstituted by identical or different substituents from the series comprising fluorine, chlorine, bromine, methyl and/or ethyl, or $R^6$ particularly preferably represents heterocyclyl having 2 to 9 carbon atoms and 1 to 3 identical or different hetero atoms, such as nitrogen, oxygen and/or sulphur, in the heterocycle, which can be monosubstituted to trisubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl, which, in turn, can be monosubstituted to trisubstituted by identical or different substituents from the series comprising fluorine, chlorine, bromine, methyl and/or ethyl.

$R^7$ particularly preferably represents phenyl which can be monosubstituted to trisubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl, which, in turn, can be monosubstituted to trisubstituted by identical or different substituents from the series comprising fluorine, chlorine, bromine, methyl and/or ethyl.

$R^2$ and $R^3$ together with the carbon atoms to which they are bonded also particularly preferably represent a five- or six-membered ring which can contain one or two hetero atoms, such as nitrogen, oxygen and/or sulphur, one or two keto groups and an $SO_2$ group, and which is optionally substituted by methyl, ethyl or a fused benzene ring.

Z represents oxygen or sulphur.

$X^1$ particularly preferably represents fluorine, chlorine or bromine.

$X^2$ particularly preferably represents fluorine, chlorine or bromine.

$R^1$ very particularly preferably represents hydrogen, methyl, ethyl, n-propyl, i-propyl, n-butyl, isobutyl and sec. butyl.

$R^2$ very particularly preferably represents hydrogen, methyl, ethyl, n-propyl, i-propyl, n-butyl, i-butyl, sec.-butyl and tert.-butyl.

$R^3$ represents a radical of the formula

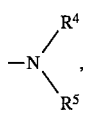

-Z-$R^6$ or -$SO_2$-$R^7$.

$R^4$ very particularly preferably represents hydrogen, methyl, ethyl, n- or i-propyl, n-, i-, s- or t-butyl, allyl, propargyl, hydroxyethyl, methoxyethyl, ethoxyethyl, hydroxypropyl, methoxypropyl, ethoxypropyl, formyl, acetyl, propionyl, methoxycarbonyl, ethoxycarbonyl, methoxy, ethoxy, n- or i-propoxy, cyclopropyl, cyclopentyl, cyclohexyl or cyclohexenyl.

$R^5$ very particularly preferably represents hydrogen, methyl, ethyl, n- or i-propyl, n-, i-, s- or t-butyl, hydroxyethyl, methoxyethyl, ethoxyethyl, hydroxypropyl, methoxypropyl, ethoxypropyl, formyl, acetyl, propionyl, trifluoroacetyl, methoxycarbonyl, ethoxycarbonyl, methylsulphonyl or ethylsulphonyl, or represents benzoyl which can be monosubstituted or disubstituted by identical or different substituents from the series comprising fluorine, chlorine, bromine, cyano, nitro, methyl, ethyl, nor i-propyl, n-, i-, s- or t-butyl, methoxy, ethoxy, n- or i-propoxy, n-, i-, s- or t-butoxy, methylthio. ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl, or $R^5$ very particularly preferably represents phenylsulphonyl which can be monosubstituted or disubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl, or $R^5$ very particularly preferably represents furanylcarbonyl which can be monosubstituted or disubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl.

$R^4$ and $R^5$ together with the nitrogen atom to which they are bonded also very particularly preferably represent a radical of the formula

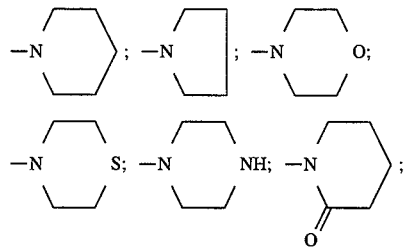

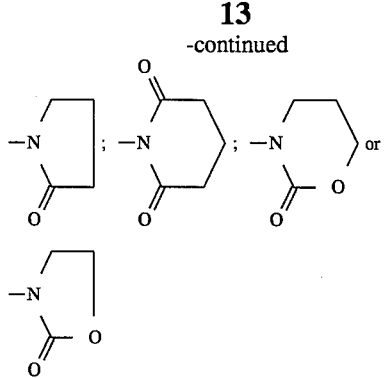

it being possible for each of these heterocycles to be monosubstituted or disubstituted by methyl.

$R^6$ very particularly preferably represents hydrogen, methyl, ethyl, n- or i-propyl, n-, i-, s- or t-butyl, allyl, propargyl, hydroxyethyl, methoxyethyl, ethoxyethyl, hydroxypropyl, methoxypropyl, ethoxypropyl, trifluoromethyl, trifluoroethyl, formyl, acetyl, propionyl, methoxycarbonylmethyl, ethoxycarbonylmethyl, cyclohexyl or cyclohexenyl, or represents phenyl, which can be monosubstituted or disubstituted by identical or different substituents from the series comprising fluorine, chlorine, bromine, cyano, nitro, methyl, ethyl, n- or i-propyl, n-, i-, s- or t-butyl, methoxy, ethoxy, nor i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl, or $R^6$ very particularly preferably represents benzyl which can be monosubstituted or disubstituted in the phenyl moiety by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl, or $R^6$ particularly preferably represents furfuryl which can be monosubstituted or disubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl, or $R^6$ very particularly preferably represents benzoyl which can be monosubstituted or disubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl, or $R^6$ very particularly preferably represents furanylcarbonyl which can be monosubstituted or disubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl, or $R^6$ very particularly preferably represents furanyl which can be monosubstituted or disubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl.

$R^7$ very particularly preferably represents phenyl which can be monosubstituted or disubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl.

$R^2$ and $R^3$ together with the carbon atom to which they are bonded also very particularly preferably represent a five- or six-membered ring which can contain one or two hetero atoms, such as nitrogen, oxygen and/or sulphur, one or two keto groups and an $SO_2$ group, and which is optionally substituted by methyl or a fused benzene ring.

Z represents oxygen or sulphur.

$X^1$ very particularly preferably represents fluorine or chlorine.

$X^2$ very particularly preferably represents fluorine or chlorine.

The substituted pyridine-4-carboxamides which are listed in the table below may be mentioned as examples of substances according to the invention.

TABLE 1

| $R^1$ | $R^2$ | $R^3$ | $X^1$ | $X^2$ |
|---|---|---|---|---|
| $CH_3$ | H | OH | Cl | Cl |
| $CH_3$ | H | $OCH_3$ | Cl | Cl |
| $CH_3$ | H | $-N(CH_3)-C(=O)-H$ | Cl | Cl |
| $CH_3$ | H | $-NH-COOCH_3$ | Cl | Cl |
| H | $CH_3$ | $-NH-COOCH_3$ | Cl | Cl |
| H | $i-C_3H_7$ | $-NH-COOCH_3$ | Cl | Cl |
| H | $i-C_4H_9$ | $-NH-COOCH_3$ | Cl | Cl |
| H | H | $-O-C_2H_5$ | Cl | Cl |
| H | H | $-O-nC_3H_7$ | Cl | Cl |
| H | H | $-O-iC_3H_7$ | Cl | Cl |
| H | H | $-O-CH_2-CH_2-OH$ | Cl | Cl |
| H | H | $-O-CH_2-CH_2-OCH_3$ | Cl | Cl |
| H | H | $-O-CH_2-CH=CH_2$ | Cl | Cl |

TABLE 1-continued $$\begin{array}{c} X^1 \\ \diagdown \\ N \\ \diagup \\ X^2 \end{array} \!\!\!\!\!\!\!\!\!\!\!\!\!\!\!\! \begin{array}{c} O \\ \| \\ C - N - CH \\ | \quad\ \ \diagdown \\ R^1 \quad\ R^3 \end{array} \!\!\!\!\!\!\!\!\! R^2 \qquad (I)$$

| R¹ | R² | R³ | X¹ | X² |
|---|---|---|---|---|
| H | H | —O—⟨cyclohexyl, H⟩ | Cl | Cl |
| H | H | —O—⟨phenyl⟩ | Cl | Cl |
| H | H | —O—CH₂—COOCH₃ | Cl | Cl |
| H | H | —S—⟨phenyl⟩ | Cl | Cl |
| H | H | —SCH₃ | Cl | Cl |
| H | H | —SC₂H₅ | Cl | Cl |
| H | H | —S—nC₃H₇ | Cl | Cl |
| H | H | —S—iC₃H₇ | Cl | Cl |
| H | H | —S—CH₂—⟨phenyl⟩ | Cl | Cl |
| H | H | —O—CH₂—⟨furyl⟩ | Cl | Cl |
| H | H | $-\overset{}{\underset{C_2H_5}{N}}-\overset{O}{\overset{\|}{C}}-H$ | Cl | Cl |
| H | H | $-\overset{}{\underset{CH_2-CH_2-OCH_3}{N}}-\overset{O}{\overset{\|}{C}}-H$ | Cl | Cl |
| H | H | $-\overset{}{\underset{OCH_3}{N}}-\overset{O}{\overset{\|}{C}}-H$ | Cl | Cl |
| H | H | $-\underset{\underset{OCH_3}{|}}{N}-COOCH_3$ | Cl | Cl |
| H | H | $-\underset{\underset{O}{\|}}{\overset{}{C}}-CH_2-CH_2-CH_2-$ | Cl | Cl |
| H | H | $-\underset{\underset{O}{\|}}{\overset{}{C}}-O-CH_2-CH_2-$ | Cl | Cl |
| H | H | $\diagdown\!\!\!\!\!\!\!\!\!\!\!\! \begin{array}{c} C=O \\ -C \\ \| \\ O \end{array}\!\!\!\!\!\!\!\!\!\!\! \diagup$ (phthaloyl) | Cl | Cl |
| H | H | $\diagdown\!\!\!\!\!\!\!\!\!\!\!\! \begin{array}{c} SO_2 \\ -C \\ \| \\ O \end{array}\!\!\!\!\!\!\!\!\!\!\! \diagup$ (saccharinyl) | Cl | Cl |

If, for example, 2,6-dichloropyridine-4-carboxamide and N-methyl-N-hydroxymethyl-formamide are used as starting substances, the course of the reaction of process (a) according to the invention can be represented by the following equation:

[2,6-dichloropyridine-4-carboxamide] + [HO—CH₂—N(CH₃)—C(=O)—H] $\xrightarrow[-H_2O]{H_2SO_4/CH_3COOH}$ [2,6-dichloropyridine-4-C(=O)—NH—CH₂—N(CH₃)—C(=O)H]

If, for example, 2,6-dichloropyridine-4-carboxamide and formaldehyde are used as starting substances, the course of the reaction of process (b) according to the invention can be represented by the following equation:

[2,6-dichloropyridine-4-carboxamide] + H—CH=O ⟶

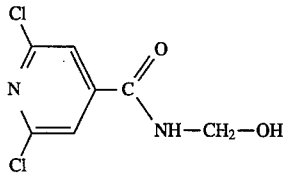

If, for example, N-(hydroxymethyl)-2,6-dichloropyridine-4-carboxamide and benzyl alcohol are used as starting substances, the course of the reaction of process (c) according to the invention, variant α, can be represented by the following equation:

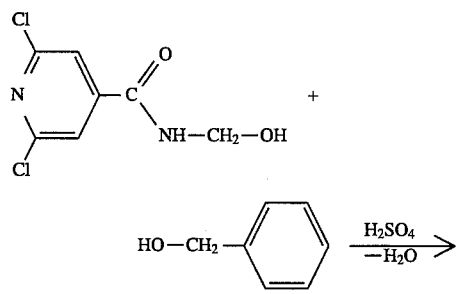

If, for example, N-(hydroxymethyl)-2,6-dichloropyridine-4-carboxamide and acetic anhydride are used as starting substances and 4-dimethylaminopyridine is used as reaction auxiliary, the course of process (c) according to the invention, variant β, can be illustrated by the following equation:

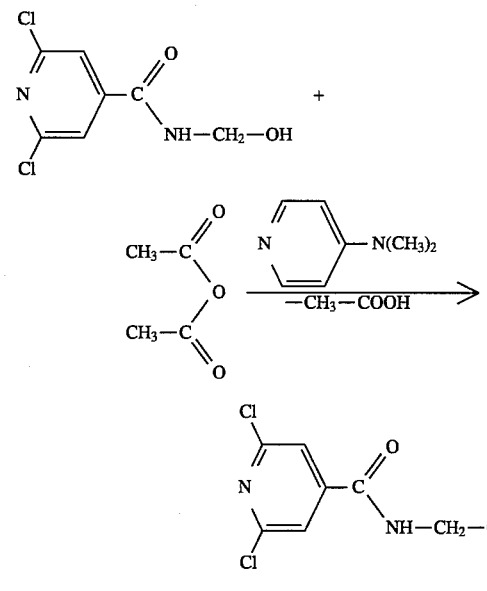

If, for example, N-(hydroxymethyl)-2,6-dichloropyridine-4-carboxamide and dimethylamine are used as starting substances, the course of process (c) according to the invention, variant γ, can be illustrated by the following equation:

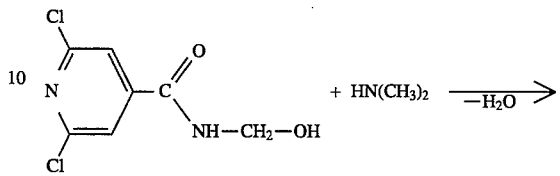

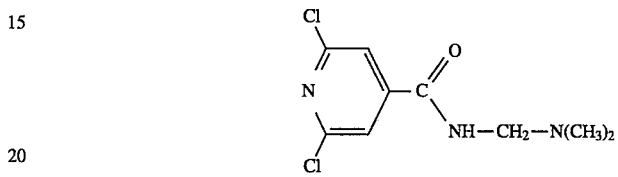

If, for example, N-(hydroxymethyl)-2,6-dichloropyridine-4-carboxamide and sodium benzenesulphinate are used as starting substances, the course of process (c) according to the invention, variant γ, can be illustrated by the following equation:

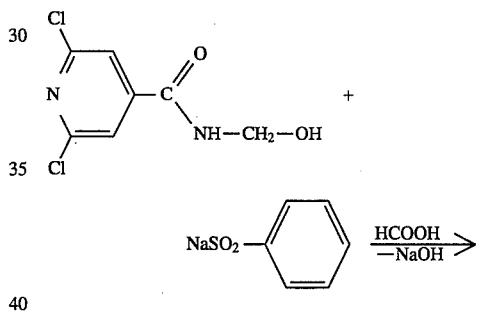

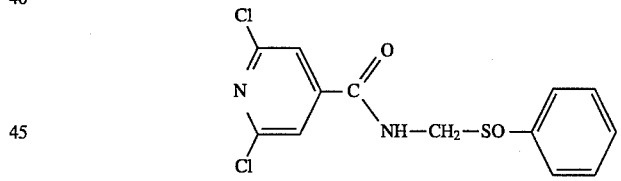

If, for example, 2-[N-(2,6-dichloropyridine- 4-yl-carbonyl)-amino]- acetamide and methanol are used as starting substances and a mixture of sodium methylate and bromine is used as reaction auxiliary, the course of the reaction in process (d) according to the invention can be represented by the following equation:

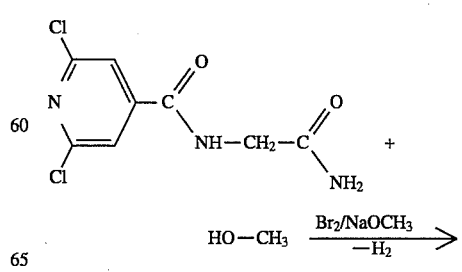

-continued

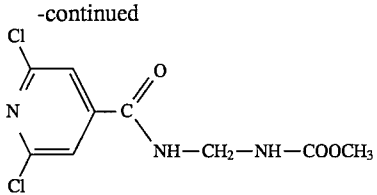

If, for example, 2,6-dichloropyridine-4-carboxylic acid chloride and aminodimethyl ether are used as starting substances, the course of the reaction in process (e) according to the invention can be represented by the following equation:

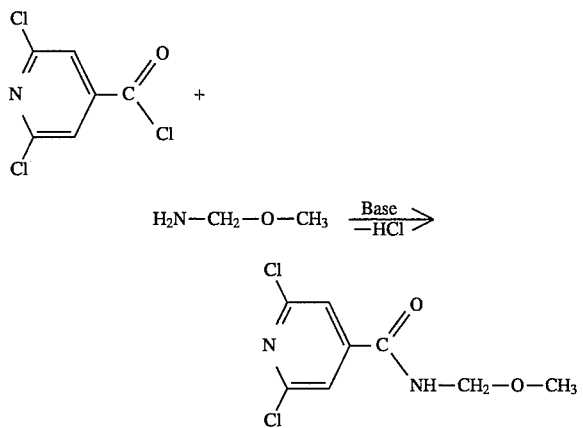

The pyridine-4-carboxamides of the formula (II) which are required as starting substances for carrying out processes (a) and (b) according to the invention are known or can be prepared in a simple manner by processes known in principle (cf. EP-OS (European Published Specification) 0,334, 812 and Synthesis 1984, 218).

Formula (III) provides a general definition of the compounds furthermore required as starting substances for carrying out process (a) according to the invention. In this formula (III), $R^2$ and $R^3$ preferably represent those radicals which have already been mentioned above as being preferred, or particularly preferred, for these substituents.

$E^1$ preferably represents hydroxyl, methoxy, acetoxy, chlorine, bromine, iodine, trimethylammonium, phenylsulphonyl, p-toluenesulphonyl or 4-chlorophenylsulphonyl.

The compounds of the formula (III) are known or can be prepared in a simple manner by processes known in principle.

The aldehydes of the formula (IV) which are required as reactants for carrying out process (b) according to the invention are also known.

The substituted pyridine-4-carboxamides which are required as starting substances for carrying out process (c) according to the invention are substances according to the invention which can be prepared, for example, by process (a) or (b) according to the invention.

Formula (V) provides a general definition of the carbinols or mercaptans required as reactants for carrying out process (c) according to the invention, variant α. In this formula, Z represents oxygen and sulphur. $R^8$ represents, besides hydrogen, preferably those radicals which have been mentioned for $R^6$ as being preferred or particularly preferred. The carbinols or mercaptans of the formula (V) are known.

Formula (VI) provides a general definition of the acid anhydrides required as reactants for carrying out process (c) according to the invention, variant β. In this formula, $R^9$ preferably represents alkyl having 1 to 6 carbon atoms, aryl having 6 to 10 carbon atoms, it being possible for the aryl moiety to be monosubstituted to trisubstituted by identical or different substituents from the series comprising halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or by phenyl which, in turn, can be monosubstituted to trisubstituted by identical or different substituents from the series comprising halogen and/or alkyl having 1 to 4 carbon atoms, or $R^9$ preferably represents heterocyclyl having 2 to 9 carbon atoms and 1 to 4 identical or different hetero atoms, such as nitrogen, oxygen and/or sulphur, in the heterocycle, which can be monosubstituted to trisubstituted by identical or different substituents from the series comprising halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoxyiminoalkyl having 1 to 4 carbon atoms in the alkoxy moiety and 1 to 4 carbon atoms in the alkyl moiety, and/or by phenyl which, in turn, can be monosubstituted to trisubstituted by identical or different substituents from the series comprising halogen and/or alkyl having 1 to 4 carbon atoms.

$R^9$ particularly preferably represents alkyl having 1 to 4 carbon atoms, phenyl which can be monosubstituted to trisubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl, and/or phenyl, which, in turn, can be monosubstituted to trisubstituted by identical or different substituents from the series comprising fluorine, chlorine, bromine, methyl and/or ethyl, or $R^9$ particularly preferably represents heterocyclyl having 2 to 9 carbon atoms and 1 to 3 identical or different hetero atoms, such as nitrogen, oxygen and/or sulphur, in the heterocycle, which can be monosubstituted to trisubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl, and/or phenyl, which, in turn, can be monosubstituted to trisubstituted by identical or different substituents from the series comprising fluorine, chlorine, bromine, methyl and/or ethyl.

$R^9$ very particularly preferably represents methyl or ethyl, or represents phenyl which can be monosubstituted or disubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl, or $R^9$ very particularly preferably represents furanyl which can be monosubstituted or disubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and/or phenyl.

The acid anhydrides of the formula (VI) are known or can be prepared in a simple manner by processes known in principle.

Formula (VII) provides a general definition of the mines required for carrying out process (c) according to the invention, variant γ. In this formula, $R^4$ and $R^5$ preferably represent those radicals which have already been mentioned above as being preferred, or particularly preferred, for these substituents.

The amines of the formula (VII) are known or can be prepared in a simple manner by processes known in principle.

Formula (VIII) provides a general definition of the sulphinic acid derivatives which are furthermore possible as reactants for carrying out process (c) according to the invention, variant γ. In this formula, $R^7$ preferably represents those radicals which have already been mentioned above as being preferred, or particularly preferred, for this substituent. X preferably represents hydrogen, sodium or potassium.

The sulphinic acid derivatives of the formula (VIII) are known or can be prepared in a simple manner by processes known in principle.

Formula (IX) provides a general definition of the pyridine-4-carboxamide derivatives required as starting substances for carrying out process (d) according to the invention. In this formula, $R^1$, $R^2$, $X^1$ and $X^2$ preferably represent those radicals which have already been mentioned above as being preferred, or particularly preferred, for these substituents.

The pyridine-4-carboxamide derivatives of the formula (IX) are known or can be prepared in a simple manner by processes known in principle (cf. U.S. Pat. No. 4,195,984 and JP-OS (Japanese Published Specification) 63-301,868).

Formula (X) provides a general definition of the alcohols required as reactants for carrying out process (d) according to the invention. In this formula, $R^{10}$ preferably represents straight-chain or branched alkyl having 1 to 6 carbon atoms, in particular straight-chain or branched alkyl having 1 to 4 carbon atoms.

The alcohols of the formula (X) are generally known compounds of organic chemistry.

Formula (XI) provides a general definition of the pyridine-4-carboxylic acid derivatives required as starting substances for carrying out process (e) according to the invention. In this formula, $X^1$ and $X^2$ preferably represent those radicals which have already been mentioned above as being preferred, or particularly preferred, for these substituents.

$E^2$ preferably represents halogen, in particular chlorine or bromine or another customary radical which activates carboxylic acid, such as, for example, an anhydride radical.

The pyridine-4-carboxylic acid derivatives of the formula (XI) are known or can be prepared in a simple manner by processes known in principle (cf. DE-OS (German Published Specification) 3,615,293 and DE-OS (German Published Specification) 2,263,026).

Formula (XII) provides a general definition of the amines furthermore required as starting substances for carrying out process (e) according to the invention. In this formula, $R^1$, $R^2$, $R^3$ preferably represent those radicals which have already been mentioned above as being preferred, or particularly preferred, for these substituents.

The amines of the formula (XII) are known or can be prepared in a simple manner by processes known in principle (cf. DE-OS (German Published Specification) 3,9318, 287; J. Heterocycl. Chem. 16, 339 (1979); Latv. PSR Zinat. Akad. Vestis Khim. Ser. 5, 563–568 (1975) and Chem. Abstr. 84, 30 179s).

Suitable diluents for carrying out process (a) according to the invention are inert organic solvents. These preferably include aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxane, tetrahydrofuran or ethylene glycol dimethyl ether or ethylene glycol diethyl ether; ketones, such as acetone or butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide, esters, such as methyl acetate or ethyl acetate, carboxylic acids, such as formic acid or acetic acid, alcohols, such as methanol, ethanol, n- or i-propanol, ethylene glycol, ethylene glycol monomethyl ether or ethylene glycol monoethyl ether, sulphoxides, such as dimethyl sulphoxide, or water.

Process (a) according to the invention is preferably carried out in the presence of a suitable reaction auxiliary. Suitable reaction auxiliaries are, preferably, strong mineral acids, such as, for example, sulphuric acid or hydrochloric acid, or else strongly acidic ion exchangers.

When carrying out process (a) according to the invention, the reaction temperatures can be varied within a substantial range. In general, the process is carried out at temperatures between 0° C. and 150° C., preferably at temperatures between 40° C. and 100° C.

To carry out process (a) according to the invention, 1.0 to 5.0 mol, preferably 1.0 to 2.5 mol, of compound of the formula (III) and, if appropriate, 1.0 to 5.0 mol, preferably 1.0 to 2.5 mol, of acid used as reaction auxiliary are generally employed per mol of pyridine-4-carboxamide of the formula (II). The reaction is carried out and the reaction products are worked up and isolated by known processes (compare Synthesis 1973, 703; Tetrahedron 46, 1791 [1990] or the preparation examples).

Process (b) according to the invention is preferably carried out in the presence of a suitable diluent. The following can preferably be used: water, alcohols, such as methanol, ethanol, n- or i-propanol, ethylene glycol, ethylene glycol monomethyl ether or ethylene glycol monoethyl ether, ethers which are miscible with water, such as dioxane, tetrahydrofuran, ethylene glycol dimethyl ether or diethylene glycol dimethyl ether, nitriles, such as acetonitrile or propionitrile, esters, such as ethyl acetate, carboxylic acids, such as formic acid or acetic acid or mixtures of these. Mixtures of water with alcohols are particularly preferably used.

Reaction auxiliaries which are suitable for carrying out process (b) according to the invention are all reaction accelerators which are customary for reactions of this type. The following can preferably be used: alkali metal carbonates, such as sodium carbonate or potassium carbonate, and furthermore alkali metal hydroxides, such as sodium hydroxide or potassium hydroxide, and furthermore carboxylic acids, such as formic acid.

When carrying out process (b) according to the invention, the reaction temperatures can be varied within a substantial range. In general, the process is carried out at temperatures between $-20°$ C. and $+120°$ C., preferably at temperatures between $0°$ C. and $+100°$ C.

To carry out process (b) according to the invention, 1.0 to 5.0 mol, preferably 1.0 to 2.5 mol, of aldehyde of the formula (IV) and a catalytic amount of reaction auxiliary are generally employed per mol of pyridine-4-carboxamide of the formula (II). Working-up is carried out by customary methods. In general, a procedure is followed in which the reaction mixture is filtered, the filtrate is concentrated, and the residue obtained is freed from any remaining impurities by treatment with suitable solvents (cf. Synthesis 1973, 703, Tetrahedron 46, 1791 (1990) and preparation examples).

Suitable diluents for carrying out process (c) according to the invention, variant α, are all inert organic solvents. The following can preferably be used: aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxane, tetrahydrofuran or ethylene glycol dimethyl ether or ethylene glycol diethyl ether; ketones, such as acetone or butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide, esters, such as methyl acetate or ethyl acetate, carboxylic acids, such as acetic acid, alcohols, such as methanol, ethanol, n- or i-propanol, ethylene glycol, ethylene glycol monomethyl ether or ethylene glycol monoethyl ether, sulphoxides, such as dimethyl sulphoxide, or water.

Process (c) according to the invention, variant α, is preferably carried out in the presence of a suitable reaction auxiliary. Suitable reaction auxiliaries are, preferably, strong mineral acids, such as, for example, sulphuric acid or hydrochloric acid, or else highly acidic ion exchangers.

When carrying out process (c) according to the invention, variant α, the reaction temperatures can be varied within a substantial range. In general, the process is carried out at temperatures between $0°$ C. and $150°$ C., preferably at temperatures between $40°$ C. and $100°$ C.

To carry out process (c) according to the invention, variant α, 1.0 to 5.0 mol, preferably 1.0 to 2.5 mol, of compound of the formula (V) and, if appropriate, 1.0 to 5.0 mol, preferably 1.0 to 2.5 mol, of acid used as reaction auxiliary or a suitable amount of acidic ion exchanger are generally employed per mol of substituted pyridine-4-carboxamide of the formula (Ia).

Working-up is carried out by customary methods (cf. Tetrahedron 46, 1791 (1990) and Synthesis 1973, 703).

Diluents which are suitable for carrying out process (c) according to the invention, variant β, are inert organic solvents. The following can preferably be used: aliphatic, alicyclic or aromatic, optionally halogenated hydrocarbons, such as benzine, benzene, toluene, xylene, chlorobenzene, dichlorobenzene, petroleum ether, hexane, cyclohexane, dichloromethane, chloroform or carbon tetrachloride, moreover ethers, such as diethyl ether, di-isopropyl ether, dioxane, tetrahydrofuran, ethylene glycol dimethyl ether or ethylene glycol dimethyl ether or ethylene glycol diethyl ether, and furthermore esters, such as methyl acetate and ethyl acetate.

Suitable reaction auxiliaries for carrying out process (c) according to the invention, variant β, are all reaction accelerators which are customary for reactions of this type. Organic bases, such as pyridine or 4-dimethylamino-pyridine, can preferably be used.

When carrying out process (c) according to the invention, variant β, the reaction temperatures can be varied within a certain range. In general, the process is carried out at temperatures between $-10°$ C. and $100°$ C., preferably between $0°$ C. and $80°$ C.

To carry out process (c) according to the invention, variant β, 1.0 to 5.0 mol, preferably 1.0 to 2.5 mol, of acid anhydride of the formula (VI) and, if appropriate, 1.0 to 5.0 mol, preferably 1.0 to 2.5 mol, of reaction auxiliary are generally employed per mol of substituted pyridine-4-carboxamide of the formula (Ia). Working-up is carried out by customary methods. In general, a procedure is followed in which the reaction mixture is filtered, the filtrate is washed to neutrality, dried and then concentrated. If appropriate, the product obtained can be freed from any remaining impurities by customary methods.

Diluents which are suitable for carrying out process (c) according to the invention, variant γ, are, if amines of the formula (VII) are employed as reactants, inert organic solvents. All those diluents which have already been mentioned in connection with the description of variant β of process (c) according to the invention can preferably be used. If sulphinic acid derivatives of the formula (VIII) are used as reactants, then organic acids, such as formic acid or acetic acid, are preferably suitable as diluents. Furthermore, those solvents which have already been mentioned in connection with the description of variant β of process (c) according to the invention are also suitable.

Reaction auxiliaries which are suitable for carrying out process (c) according to the invention, variant γ, are all reaction accelerators which are customary for reactions of this type. Organic acids, such as formic acid or acetic acid, can preferably be used.

When carrying out process (c) according to the invention, variant γ, the reaction temperatures can, again, be varied within a substantial range. In general, the process is carried out at temperatures between $0°$ C. and $150°$ C., preferably between $40°$ C. and $120°$ C.

To carry out process (c) according to the invention, variant γ, 1.0 to 5.0 mol, preferably 1.0 to 2.5 mol, of amine of the formula (VII) or sulphinic acid derivative of the formula (VIII) and a catalytic or else a larger amount of reaction auxiliary are generally employed per mol of substituted pyridine-4-carboxamide of the formula (Ia). Working-up is carried out by customary methods (cf. also preparation examples).

In a specific variant, processes (b) and (c) according to the invention can be carried out in succession in the form of a one-pot reaction, where isolation of the substituted pyridine-4-carboxamides which are initially formed is dispensed with.

Oxidants which can be employed for carrying out process (d) according to the invention are all oxidizing substances which are customary for reactions of this type ("Hofmann Degradation"). The following can preferably be used: sodium hypochlorite or sodium hypobromite, lead tetraacetate or I,I-bis[trifluoroacetoxy]-iodobenzene.

Suitable diluents for carrying out process (d) according to the invention are inert organic solvents. The following can preferably be used: aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxane, tetrahydrofuran or ethylene glycol dimethyl ether or ethylene glycol diethyl ether; nitriles, such as acetonitrile, propionitrile or benzonitrile; however, particularly preferably the alcohol used as reactant, such as methanol, ethanol, n- or i-propanol, ethylene glycol monomethyl ether or ethylene glycol monoethyl ether.

When carrying out process (d) according to the invention, the reaction temperatures can be varied within a substantial range. In general, the process is carried out at temperatures between −70° C. and +120° C., preferably at temperatures between −20° C. and +40° C.

To carry out process (d) according to the invention, 1.0 to 100 mol of alcohol of the formula (X), preferably simultaneously as the diluent, and, if appropriate, 1.0 to 5.0 mol, preferably 1.0 to 2.5 mol, of oxidant are generally employed per mol of the pyridine-4-carboxamide derivative of the formula (IX).

Working-up is carried out by customary methods (cf. Chem. Commun. 1982, 280, DE-OS (German Published Specification) 3,728,277, and the preparation examples).

Suitable diluents for carrying out process (e) according to the invention are inert organic solvents. The following can preferably be used: aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxane, tetrahydrofuran or ethylene glycol dimethyl ether or ethylene glycol diethyl ether; ketones, such as acetone or butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide, esters, such as methyl acetate or ethyl acetate, or sulphoxides, such as dimethyl sulphoxide.

Suitable reaction auxiliaries for carrying out process (e) according to the invention are acid-binding agents. All customary inorganic and organic bases can be used. The following can preferably be used: alkaline earth metal hydroxides or alkali metal hydroxides, such as sodium hydroxide, calcium hydroxide, potassium hydroxide or else ammonium hydroxide, alkali metal carbonates, such as sodium carbonate, potassium carbonate, potassium hydrogencarbonate, sodium hydrogencarbonate or ammonium carbonate, alkali metal acetates or alkaline earth metal acetates, such as sodium acetate, potassium acetate, calcium acetate or ammonium acetate, and also tertiary amines, such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

When carrying out process (e) according to the invention, the reaction temperatures can be varied within a substantial range. In general, the process is carried out at temperatures between −20° C. and +120° C., preferably at temperatures between 0° C. and +40° C.

To carry out process (e) according to the invention, 1.0 to 5.0 mol, preferably 1.0 to 2.5 mol, of amine of the formula (XII) and, if appropriate, 1.0 to 5.0 mol, preferably 1.0 to 2.5 mol, of reaction auxiliary are generally employed per mol of pyridine-4-carboxylic acid derivative of the formula (XI). Working-up is carried out by customary methods.

Compounds of the formula (I) which have been prepared by processes (a) to (e) according to the invention, in which the substituent $R^3$ represents a hydroxyl group or a primary or secondary amino group, can be acylated or sulphonylated on the hydroxyl or amino group by customary methods using acylating agents or sulphonylating agents, respectively, if appropriate in the presence of a suitable diluent and if appropriate in the presence of a customary reaction auxiliary.

The active substances according to the invention have a powerful resistance-inducing action in plants. They are therefore suitable for generating resistance in plants against attack by undesired microorganisms.

Resistance-inducing substances are to be understood as meaning, in the present context, substances which, on the one hand, display only a low degree of activity when acting directly on the undesired microorganisms but which, on the other hand, are capable of stimulating the defence system of plants in such a way that when the treated plants are subsequently inoculated with undesired microorganisms, these plants show a high level of resistance to these microorganisms.

Undesired microorganisms are to be understood as meaning, in the present case, phytopathogenic fungi, bacteria and viruses. This means that the substances according to the invention can be employed for generating, within a certain period after treatment, resistance in plants against attack by the pathogens mentioned. The period in which resistance is generated generally extends over 1 to 10 days, preferably 1 to 7 days, after the plants have been treated with the active compounds.

Microorganisms which are undesired in crop protection are fungi from the classes of the Plasmodiophoromycetes, Oomycetes, Chytridiomycetes, Zygomycetes, Ascomycetes, Basidiomycetes and Deuteromycetes.

Some causative organisms of fungal, bacterial and vital diseases which come under the generic names listed above may be mentioned as examples, but not by way of limitation:

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *Peronospora brassicae;*

Erysiphe species, such as, for example, *Erysiphe graminis;*

Spaerotheca species, such as, for example, *Spaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *Pyrenophora graminea* (conidia form: Drechslera sp., syn: Helminthosporium sp.);

Cochliobolus species, such as, for example, *Cochliobolus sativus* (conidia form: Drechslera sp., syn: Helminthosporium sp.);

Uromyces species, such as, for example, *Uromyces phaseoli;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum* or *Fusarium graminearum;*

Botrytis species, such as, for example, *Botrytis cinerea;*

Leptosphaeria species, such as, for example, *Leptosphaeria nodorum* or *Leptosphaeria tritici* (conidia form: Septoria sp.);

Leptosphaeria species, such as, for example, *Leptosphaeria maculans* (conidia form: *Phoma lingam*);

Cercospora species, such as, for example, *Cercospora canescens* or *Cercospora beticola;*

Alternaria species, such as, for example, *Alternaria brassicae;* and

Pseudocercosporella species, such as, for example, *Pseudocercosporella herpotrichoides.*

The good toleration, by plants of the active compounds, at the concentrations required for inducing disease resistance in plants, permits treatment of above-ground parts of plants, of vegetative propagation stock and seeds, and of the soil.

In this context, the active compounds according to the invention can be employed particularly successfully for preventing the occurrence of cereal diseases, such as, for example, powdery mildew of cereals (*Erysiphe graminis*), leaf stripe of barley (*Pyrenophora graminea*), spot blotch of cereals (*Cochliobolus sativus*), net blotch of barley (*Pyrenophora teres*), Septoria disease of cereals (*Septoria nodorum, Septoria tritici*), Fusarium diseases (*Fusarium culmorum, Fusarium graminearum*), cereal rusts, (*Puccinia recondite, Puccinia graminis, Puccinia glumarum*), for preventing the occurrence of rice diseases caused by, for example, *Pyricularia oryzae* or *Pellicularia sasakii,* for preventing the occurrence of fruit and vegetable diseases, such as, for example, powdery mildew on various host plants (Erysiphe sp., Sphaerotheca sp., Podosphaera sp.);

downy mildew on various host plants (Plasmopara sp., Peronospora sp., Pseudoperonospora sp., Bremia sp.);

scab on various host plants (Venturia sp.);

grey mould on various host plant (*Botrytis cinerea*).

The active compounds which can be used according to the invention are distinguished not only by an activity which induces resistance against plant diseases, but also by a nematicidal activity.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, and furthermore used with burning ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogeno hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocynanine dyestuffs, and trace nutrients, such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as mixtures with other known active compounds, such as fungicides, insecticides, bactericides, acaricides, nematicides, herbicides, bird repellant, growth regulators, plant nutrients and soil conditioners.

The following may be mentioned in this context as examples of fungicides: imazalil, benomyl, carbendazim, thiophanate-methyl, captafol, captan, sulphur, triforin, dodemorph, tridemorph, pyrazophos, furalaxyl, ethirimol, dimethirimol, bupirimat, chlorothalonil, vinclozolin, procymidon, iprodion, metalaxyl, carboxin, oxycarboxin, fenarimol, nuarimol, fenfuram, methfuroxan, nitrotalisopropyl, triadimefon, thiabendazole, etridiazole, triadimenol, bitertanol, propiconazole, anilazine, tebuconazole, biloxazole, dithianon, binapacryl, quinomethionate, guazatine, dodine, fentin-acetate, fentinhydroxide, dinocap, folpet, dichlofluanide, ditalimphos, kitazin, cycloheximide, dichlobutrazole, fenapanil, ofurace, etaconazole and fenpropemorph.

The active compounds can be used as such or in the form of their formulations or the use forms prepared therefrom by further dilution, such as ready-to-use solutions, emulsions, suspensions, powders, pastes and granules. They are used in the customary manner, for example by watering, dipping, spraying, atomizing, fogging, as a vapour-releasing product, by injecting, suspending, brushing on, dusting, scattering, as a powder for dry seed treatment, a solution or water-soluble powder for seed treatment, a water-dispersible powder for slurry treatment, or by incrusting.

When used for inducing resistance, the active compound concentrations used in the use forms for the treatment of parts of plants can be varied within a substantial range. In general, they are between 1 and 0.0001 per cent by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 1.0 per cent by weight, preferably 0.0001 to 0.02 percent by weight, are required at the place of action.

The preparation and the use of the substances according to the invention is illustrated by the examples which follow.

PREPARATION EXAMPLES

EXAMPLE 1

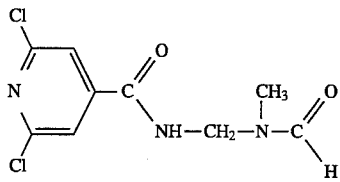
(I-1)

(Process a)

2.25 g (0,022 mol) of concentrated sulphuric acid are added dropwise with cooling and stirring at 20° C. to 25° C. to a suspension of 1.93 g (0.01 mol) of 2,6-dichloropyridine-4-carboxamide and 0.89 g (0.01 mol) of N-hydroxymethyl-N-methyl-formamide in 15 ml of glacial acetic acid (compare, for example, Synthesis 1984, 218), and the mixture is subsequently stirred for 24 hours at room temperature. For working-up, 25 ml of water are added dropwise with cooling and stirring at 20° C. to 25° C. The reaction mixture is subsequently extracted five times using 40 ml portions of dichloromethane, the combined organic extracts are dried over sodium sulphate and concentrated under reduced pressure, the oily residue is crystallized by trituration with water, and the crystals are dried.

1.63 g (62% of theory) of N-(N-methyl-N-formyl-aminomethyl)-2,6-dichloropyridine-4-carboxamide of melting point 150° to 155° C. are obtained.

EXAMPLE 2

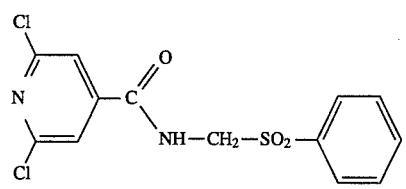
(I-2)

(Process c, variant γ)

A mixture of 1.93 g (0.01 mol) of 2,6-dichloropyridine-4-carboxamide, 0.89 g (0.011 mol) of formaline (37 per cent strength) and 2.03 g (0.012 mol) of sodium benzenesulphinate in 12 ml of formic acid is refluxed for 2.5 hours and subsequently cooled to 70° C. The reaction mixture is diluted with 50 ml of water and stirred for 15 minutes at room temperature. The precipitate which has separated out is filtered off with suction and dried. The product is recrystallized from an ethanol/chloroform/petroleum ether mixture.

1.9 g (53% of theory) of N-(benzenesulphonylmethyl)-2,6-dichloropyridine-4-carboxamide of melting point 209° to 210° C. are obtained.

EXAMPLE 3

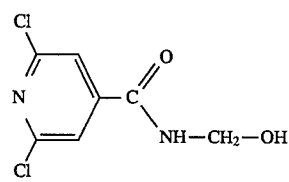
(I-3)

(Process b)

A mixture of 3.9 g (0.02 mol) of 2,6-dichloropyridine-4-carboxamide, 0.56 g (0.04 mol) of potassium carbonate and 0.36 g (0.02 mol) of water in 40 ml of ethyl acetate is refluxed for 15 minutes, 0.6 g (0.02 mol) of paraformaldehyde is subsequently added at boiling point, and the mixture is heated at the boil for a further 1 to 2 minutes. The hot solution is filtered, the filtrate is evaporated, and the residue is triturated with diethyl ether, filtered off with suction and dried.

3.75 g (85% of theory) of N-(hydroxymethyl)-2,6-dichloropyridine-4-carboxamide of melting point 155° to 157° C. (decomposition) are obtained.

EXAMPLE 4

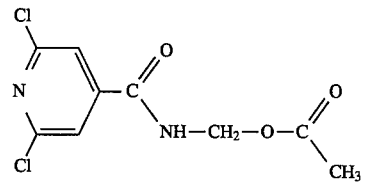
(I-4)

(Process c, variant β)

A solution of 0.63 g (0.006 mol) of acetic anhydride (97 per cent strength) in 5 ml of dichloromethane is added dropwise at 0° C. with cooling and stirring to a solution of 1.1 g (0.005 mol) of N-(hydroxymethyl)-2,6-dichloropyridine-4-carboxamide and 0.6 g (0.005 mol) of 4-dimethylaminopyridine in 10 ml of dichloromethane, and the mixture is subsequently stirred for one hour at 0° C. and one hour at room temperature. For working-up, the reaction mixture is filtered. The filtrate is washed in succession with aqueous sodium hydrogen carbonate solution and water, dried over sodium sulphate and evaporated. The residue is recrystallized from dichloromethane/petroleum ether.

0.65 g (49% of theory) of N- (acetoxymethyl)-2,6-dichloropyridine-4-carboxamide of melting point 94° to 95° C. is obtained.

EXAMPLE 5

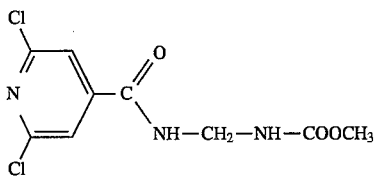
(I-5)

(Process d)

A mixture of 1.11 g (0.011 mol) of triethylamine and 2 ml of absolute methanol is added dropwise at 20° to 25° C. with stirring to a suspension of 1.25 g (0.005 mol) of $N^\alpha$-(2,6-dichloropyridine-4-carbonyl)-glycinamide and 2.19 g (0.05 mol) of [bis-(trifluoroacetoxy)-iodo]-benzene in 25 ml of absolute methanol, and the mixture is subsequently stirred for 3 hours at 30° C. For working-up, the reaction mixture is cooled to 10° C. The precipitate which has separated out is filtered off with suction and dried.

0.55 g (39% of theory) of N-(methoxycarbonylaminolemethyl)-2,6-dichloropyridine-4-carboxamide of melting point 175° to 176° C. is obtained.

Preparation of Starting Compounds

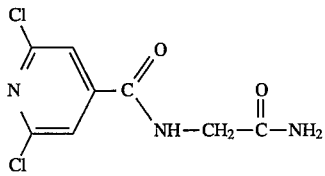
(IX-1)

Ammonia is passed at 0° C. into a suspension of 13.61 g (0.0507 mol) of N-(2,6-dichloropyridine-4-carbonyl)glycine methyl ester in 70 ml of methanol until the suspension is saturated, and the mixture is subsequently stirred for 2.5 hours at room temperature. The precipitate which has separated out is filtered off with suction, washed with methanol and dried.

10.6 g (83% of theory) of $N^\alpha$-(2,6-dichloropyridine-4-carbonyl)-glycinamide of melting point 211° to 213° C. are obtained.

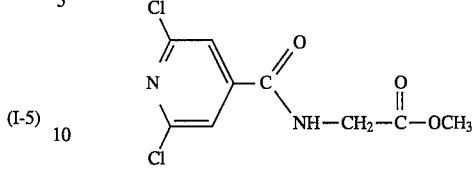

10 g (0.1 mol) of N-methylpiperidine and 13.8 g (0.1 mol) of isobutyl chloroformate are added at –20° C. to a suspension of 20.9 g (0.1 mol) of 2,6-dichloropyridine-4-carboxylic acid in 100 ml of dichloromethane, and the mixture is subsequently stirred for 10 minutes at –20° C.

The reaction mixture is cooled to –60° C., and a solution of 12.7 g (0.1 mol) of glycine methyl ester hydrochloride and 10 g of (0.1 mol) of N-methylpiperidine in 100 ml of dichloromethane is then added in one portion, and the mixture is stirred for a further 2 hours at –15° C. and then for 18 hours at room temperature, For working-up, the reaction mixture is washed in succession with 1-molar aqueous citric acid, aqueous sodium hydrogen carbonate solution and water, dried over sodium sulphate and evaporated under reduced pressure. The residue is recrystallized from chloroform/petroleum ether.

12.5 g (46% of theory) of N-(2,6-dichloropyridine-4-carbonyl)-glycine methyl ester of melting point 140° to 141° C. are obtained.

The substituted pyridine-4-carboxamides of the formula (I) which are listed in Table 2 below are synthesized by the methods described above and the general preparation instructions.

TABLE 2

(I)

| Ex. No. | Comp. No. | $R^1$ | $R^2$ | $R^3$ | $X^1$ | $X^2$ | Melting Point/°C. |
|---------|-----------|-------|-------|-------|-------|-------|-------------------|
| 6 | (I-6) | H | H | –N(CH$_3$)$_2$ | Cl | Cl | Oil |
| 7 | (I-7) | H | H | –SO$_2$–C$_6$H$_4$–CH$_3$ | Cl | Cl | 217–219 |

TABLE 2-continued $$\begin{array}{c} X^1 \\ | \\ N \end{array} \underset{X^2}{\overset{}{\bigcirc}} C \overset{O}{\underset{R^1}{\overset{\|}{-}}} N - \overset{R^2}{\underset{R^3}{\overset{|}{C}H}} \qquad (I)$$

| Ex. No. | Comp. No. | $R^1$ | $R^2$ | $R^3$ | $X^1$ | $X^2$ | Melting Point/°C. |
|---|---|---|---|---|---|---|---|
| 8 | (I-8) | H | H | —SO$_2$—C$_6$H$_4$—Cl | Cl | Cl | 190–191 |
| 9 | (I-9) | H | H | —OCH$_3$ | Cl | Cl | 112–114 |
| 10 | (I-10) | H | H | —O—CH$_2$—C$_6$H$_5$ | Cl | Cl | 80–82 |
| 11 | (I-11) | H | H | —O—C(=O)—C$_6$H$_5$ | Cl | Cl | 122–124 |
| 12 | (I-12) | H | H | —N(CH$_3$)$_2$ | Cl | Cl | 202–204 (hydrochloride) |

Use Examples

In the use examples which follow, the compounds listed below are employed as comparison substances:

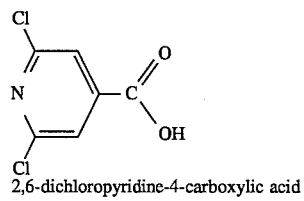

2,6-dichloropyridine-4-carboxylic acid (A)

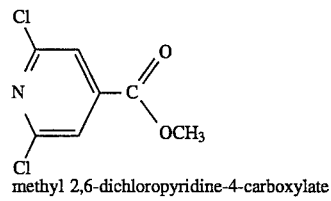

methyl 2,6-dichloropyridine-4-carboxylate (B)

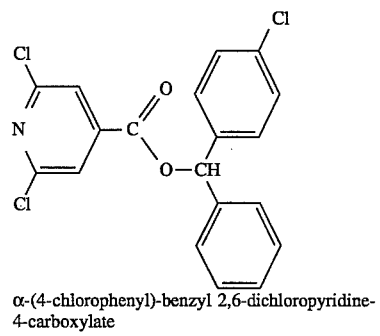

α-(4-chlorophenyl)-benzyl 2,6-dichloropyridine-4-carboxylate (C)

EXAMPLE A

Venturia-Test (Apples)/induction of resistance
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for resistance-inducing activity, young plants are sprayed with the preparation of active compound until dripping wet. 4 days after the treatment, the plants are inoculated with an aqueous conidia suspension of the pathogen causing apple scab (Venturia inaequalis) and then remain in an incubation cabin for one day at 20° C. and a relative atmospheric humidity of 100%.

The plants are then placed in a greenhouse at 20° C. and a relative atmospheric humidity of approximately 70%.

The test is evaluated 12 days after the inoculation.

In this test, a degree of effectiveness of more than 80% is shown by the substances according to the invention (I-3), (I-6), (I-7), (I-8) and (I-9) at a concentration of active compound of 100 ppm. At the same concentration, comparison compound (B) only shows a degree of effectiveness of 65%.

EXAMPLE B

Erysiphe-Test (barley)/induction of resistance
Solvent: 4.7 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for resistance-inducing activity, young plants are sprayed with the preparation of active compound until dripping wet. 4 days after the treatment, the plants are dusted with spores of *Erysiphe graminis* f. sp. hordei.

The plants are placed in a greenhouse at a temperature of approximately 20° C. and a relative atmospheric humidity of approximately 80% to promote the development of mildew pustules.

The test is evaluated 7 days after the inoculation.

In this test, a degree of effectiveness of more than 50% is shown by the substances according to the invention (I-1), (I-3), (I-9) and (I-10) at a concentration of active compound of 0.0125%. At the same concentration, comparison compound (B) only shows a degree of effectiveness of 30%.

EXAMPLE C

Phytophthora-Test (tomatoes)/induction of resistance
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for resistance-inducing activity, young plants are sprayed with the preparation of active compound until dripping wet. 4 days after the treatment, the plants are inoculated with an aqueous spore suspension of *Phytophthora infestans*.

The plants are then placed in an incubation cabin at 20° C. and a relative atmospheric humidity of approximately 100%.

The test is evaluated 3 days after the inoculation.

In this test, a degree of effectiveness of more than 75% is shown by the substances according to the invention (I-1), (I-3), (I-4), (I-6) and (I-8) to (I-11) at a concentration of active compound of 100 ppm. Comparison substances (B) and (C) only show a degree of effectiveness of 68% and 36%, respectively.

We claim:

1. A substituted pyridine-4-carboxamide of the formula

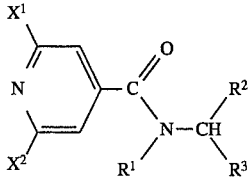

in which
- $R^1$ represents hydrogen or straight-chain or branched alkyl having 1 to 6 carbon atoms,
- $R^2$ represents hydrogen or straight-chain or branched alkyl having 1 to 6 carbon atoms,
- $R^3$ represents a radical of the formula

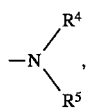

-Z-$R^6$ or -SO$_2$-$R^7$, in which
- $R^4$ represents hydrogen, straight-chain or branched alkyl having 1 to 6 carbon atoms, straight-chain or branched alkenyl having 2 to 6 carbon atoms, straight-chain or branched alkinyl having 2 to 6 carbon atoms, straight-chain or branched hydroxyalkyl having 1 to 6 carbon atoms, straight-chain or branched alkoxyalkyl having 1 to 6 carbon atoms in the alkyl moiety and 1 to 6 carbon atoms in the alkoxy moiety, alkanoyl having 1 to 6 carbon atoms in the alkane moiety, alkoxycarbonyl having 1 to 6 carbon atoms in the alkoxy moiety, alkoxy having 1 to 6 carbon atoms, formyl, cycloalkyl having 3 to 7 carbon atoms or cycloalkenyl having 3 to 7 carbon atoms,
- $R^5$ represents hydrogen, straight-chain or branched alkyl having 1 to 6 carbon atoms, straight-chain or branched hydroxyalkyl having 1 to 6 carbon atoms, straight-chain or branched alkoxyalkyl having 1 to 6 carbon atoms in the alkoxy moiety and 1 to 6 carbon atoms in the alkyl moiety, alkanoyl having 1 to 6 carbon atoms in the alkane moiety, alkylsulphonyl having 1 to 6 carbon atoms in the alkyl moiety, alkoxycarbonyl having 1 to 6 carbon atoms in the alkoxy moiety, formyl, straight-chain or branched halogenoalkanoyl having 2 to 7 carbon atoms and 1 to 13 identical or different halogen atoms, or arylcarbonyl having 6 to 10 carbon atoms in the aryl moiety, which can be monosubstituted to trisubstituted by identical or different substitutents selected from the group consisting of halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or by phenyl which, in turn, can be monosubstituted to trisubstituted by identical or different substituents selected from the group consisting of halogen and/or alkyl having 1 to 4 carbon atoms, or
- $R^5$ represents arylsulphonyl having 6 to 10 carbon atoms in the aryl moiety, which can be monosubstituted to trisubstituted by identical or different substituents selected from the group consisting of halogen, cyano, nitro, straight-chain or straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or by phenyl which, in turn, can be monosubstituted to trisubstituted by identical or different substituents selected from the group consisting of halogen, and/or alkyl having 1 to 4 carbon atoms, or
- $R^5$ represents heteroarylcarbonyl having 2 to 9 carbon atoms and 1 to 4 hereto atoms, which can be monosubstituted to trisubstituted by identical or different substituents selected from the group consisting of halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxy-carbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or by phenyl which, in turn, can be monosubstituted to trisubstituted by identical of different substituents selected from the group consisting of halogen, and/or alkyl having 1 to 4 carbon atoms, and $R^6$ represents hydrogen, straight-chain or branched alkyl having 1 to 6 carbon atoms, straight-chain or branched alkenyl having 2 to 6 carbon atoms, straight-chain or branched alkinyl having 2 to 6 carbon atoms, straight-chain or branched hydroxyalkyl having 1 to 6 carbon atoms, straight-chain or branched alkoxyalkyl having 1 to 6 carbon atoms in the alkoxy moiety and 1 to 6 carbon atoms in the alkyl moiety, alkanoyl having 1 to 6 carbon atoms in the alkane moiety, alkoxycarbonyl having 1 to 6 carbon atoms in the alkoxy moiety, straight-chain or branched halogenoalkyl having 1 to 6 carbon atoms and 1 to 13 identical or different halogen atoms, formyl, cycloalkyl having 3 to 7 carbon atoms, cycloalkenyl having 3 to 7 carbon atoms, or arylalkyl having 1 to 6 carbon atoms in the straight-chain or branched alkyl moiety and 6 to 10 carbon atoms in the aryl moiety, which can be monosubstituted to trisubstituted by identical or different substituents selected from the group consisting of halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy, having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or by phenyl which, in turn, can be monosubstituted to trisubstituted by identical of different substituents selected from the group consisting of halogen, and/or alkyl having 1 to 4 carbon atoms, or $R^6$ represents arylcarbonyl having 6 to 10 carbon atoms in the aryl moiety, which can be monosubstituted to trisubstituted by identical or different substituent selected from the group consisting of halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or by phenyl which, in turn, can be monosubstituted to trisubstituted by identical or different substituents selected from the group consisting of halogen and/or alkyl having 1 to 4 carbon atoms, or $R^6$ represents aryl having 6 to 10 carbon atoms which can be monosubstituted to trisubstituted by identical of different substituents selected from the group consisting of halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoximino-alkyl having 1 to 4 carbon atoms in the alkoxy moiety and 1 to 4 carbon atoms in the alkyl moiety, and/or by phenyl which, in turn, can be monosubstituted to trisubstituted by identical or different substituents selected from the group consisting of halogen and/or alkyl having 1 to 4 carbon atoms, $R^6$ represents heterocyclylalkyl having 1 to 6 carbon atoms in the straight-chain or branched alkyl radical and 2 to 9 carbon atoms and 1 to 4 identical or different hetero atoms, which can be monosubstituted to trisubstituted by identical or different substituents selected from the group consisting of halogen, cyano nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different, straight-chain or branched halogenoalkoxy having 1 to 4 carbon atoms and 1 to 9 identical or different, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or by phenyl which, in turn, can be monosubstituted to trisubstituted by identical or different substituents selected from the group consisting of halogen and/or alkyl having 1 to 4 carbon atoms, or $R^6$ represents heterocyclylcarbonyl having 2 to 9 carbon atoms and 1 to 4 identical or different hetero atoms, which can be monosubstituted to trisubstituted by identical or different substituents selected from the group consisting of halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or substituents selected from the group consisting of halogen and/or alkyl having 1 to 4 carbon atoms, or $R^6$ represents heterocyclyl having 2 to 9 carbon atoms and 1 to 4 identical or different hetero atoms, which can be monosubstituted to trisubstituted by identical or different substituents selected from the group consisting of halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogeno-alkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or by phenyl which, in turn, can be monosubstituted to trisubstituted by identical or different substituents from the series comprising halogen and/or alkyl having 1 to 4 carbon atoms, substituents selected from the group consisting of halogen and/or alkyl having 1 to 4 carbon atoms, $R^7$ represents aryl having 6 to 10 carbon atoms which can be monosubstituted to trisubstituted by identical of different substituents selected from the group consisting of halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy to 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or by phenyl which, in turn, can be monosubstituted to trisubstituted by identical or different substituents selected from the group consisting of halogen and/or alkyl having 1 to 4 carbon atoms, Z represents oxygen or sulphur, $X^1$ represents fluorine, chlorine, bromine or iodine and $X^2$ represents fluorine, chlorine, bromine or iodine with the proviso when $R^3$ represents $-Z-R^6$ and Z presents oxygen, $R^6$ cannot represent hydrogen or alkyl having 1 to 6 carbon atoms.

2. A compound according to claim 1, wherein such compound is N-(N-methyl-N-formyl-aminomethyl)-2,6-dichloropyridine-4-carboxamide of the formula

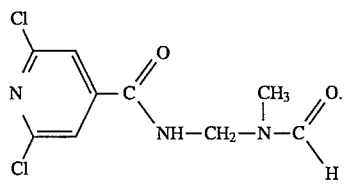

3. A plant-microbicidal composition comprising an amount effective therefor of a compound according to claim 1 and a diluent.

4. A method of combating plant pathogenic microorganisms which comprises applying to such plants or to a locus from which it is desired to exclude such microorganisms an amount effective therefor of a compound according to claim 1.

5. The method according to claim 4, wherein such compound is N-(N-methyl-N-formyl-aminomethyl)-2,6-dichloropyridine-4-carboxamide.

* * * * *

UNITED STATES PATENT AND TRADEMARK OFFICE
CERTIFICATE OF CORRECTION

PATENT NO.   : 5,583,151
DATED        : December 10, 1996
INVENTOR(S)  : Winfried Lukenheimer et al.

It is certified that error appears in the above-identified patent and that said Letters Patent is hereby corrected as shown below:

<u>Title page,</u>
Item [56], References Cited, U.S. PATENT DOCUMENTS, insert:
```
--    4,690,934    9/1987 ................514/354
      4,966,968    10/1990 .............. 514/340
      4,195,954    4/1980 ............... 71/94 --
```

FOREIGN PATENT DCUMENTS, insert:
```
-- 0334812    9/1989    EPO......... 514/354
   0334809    9/1989    EPO......... 514/354
   0332579    9/1989    EPO......... 514/354
   0268775    6/1988    EPO......... 514/354
   0246507    11/1987   EPO......... 514/354 --
```

OTHER PUBLICATIONS, insert:
-- Chemical Abstracts, Vol. 64, No. 6, Abstract 9706g, March 14, 1996, Josef Klosa.

Abstract 16203e, June 7, 1965, Enrico Kneusli and Hans Gysin --

Signed and Sealed this

Eighteenth Day of March, 2003

JAMES E. ROGAN
*Director of the United States Patent and Trademark Office*